US008742153B2

(12) United States Patent
Maniwa et al.

(10) Patent No.: US 8,742,153 B2
(45) Date of Patent: Jun. 3, 2014

(54) RUTHENIUM COMPLEX MIXTURE, METHOD OF PRODUCING THE SAME, COMPOSITION FOR FILM FORMATION, RUTHENIUM-CONTAINING FILM, AND METHOD OF PRODUCING THE SAME

(75) Inventors: Atsushi Maniwa, Kanagawa (JP); Noriaki Oshima, Kanagawa (JP); Kazuhisa Kawano, Kanagawa (JP); Taishi Furukawa, Kanagawa (JP); Hirokazu Chiba, Kanagawa (JP); Toshiki Yamamoto, Kanagawa (JP)

(73) Assignee: Tosoh Corporation, Shunan-shi, Yamaguchi (JP)

( * ) Notice: Subject to any disclaimer, the term of this patent is extended or adjusted under 35 U.S.C. 154(b) by 78 days.

(21) Appl. No.: 13/504,573

(22) PCT Filed: Nov. 29, 2010

(86) PCT No.: PCT/JP2010/071208
§ 371 (c)(1),
(2), (4) Date: Apr. 27, 2012

(87) PCT Pub. No.: WO2011/080978
PCT Pub. Date: Jul. 7, 2011

(65) Prior Publication Data
US 2012/0227625 A1    Sep. 13, 2012

(30) Foreign Application Priority Data

Dec. 28, 2009  (JP) ................................. 2009-297196
Aug. 9, 2010   (JP) ................................. 2010-178697

(51) Int. Cl.
C07F 17/02   (2006.01)
C23C 16/18   (2006.01)
H01L 21/316  (2006.01)

(52) U.S. Cl.
CPC .......... *C07F 17/02* (2013.01); *H01L 21/31695* (2013.01); *C23C 16/18* (2013.01)
USPC .................... 556/136; 106/287.18; 427/248.1

(58) Field of Classification Search
CPC .... H01L 21/31695; C07F 17/02; C23C 16/18
USPC .................... 556/136; 106/287.18; 427/248.1
See application file for complete search history.

(56) References Cited

U.S. PATENT DOCUMENTS

| 7,211,509 B1 | 5/2007 | Gopinath et al. |
| 2003/0088116 A1 | 5/2003 | Kawano et al. |
| 2004/0247911 A1 | 12/2004 | Saito |
| 2006/0211228 A1 | 9/2006 | Matsuda |
| 2006/0223310 A1 | 10/2006 | Suzuki |
| 2007/0069383 A1 | 3/2007 | Suzuki |
| 2009/0087982 A1 | 4/2009 | Wang et al. |

FOREIGN PATENT DOCUMENTS

| EP | 1 293 509 A1 | 3/2003 |
| JP | A 05-132776 | 5/1993 |
| JP | A 2003-342286 | 12/2003 |
| JP | A 2004-067601 | 3/2004 |
| JP | A 2006-036780 | 2/2006 |
| JP | A 2008-538126 | 10/2008 |
| JP | 2009-7270 | 1/2009 |
| JP | A 2009-007270 | 1/2009 |

OTHER PUBLICATIONS

International Search Report for PCT/JP2010/071208, mailed Jan. 25, 2011.
Non-English Written Opinion of the International Searching Authority for PCT/JP2010/071208, mailed Jan. 25, 2011.
Kawano et al., The Effect of Precursor Ligands on the Deposition Characteristics of Ru Films by MOCVD, *Electrochemical and Solid-State Letters*, vol. 12, No. 10, Aug. 2009, pp. D80-D83.
Kawano et al., Low-Temperature Preparation of Metallic Ruthenium Films by MOCVD Using Bis (2,4-dimethylpentadienyl) ruthenium, *Electrochemical and Solid-State Letters*, vol. 10, No. 6, 2007, pp. D60-D62.
Electrochemical and Solid-State Letters, 2003, vol. 6, No. 9, p. C117-C119.
Written Opinion in Singapore Patent Appln. No. 201204015-0 dated Jul. 22, 2013.
Extended European Search Report in EP 10 84 0837 dated Oct. 10, 2013.
Chinese Office Action and English translation in CN 201080059677.2 dated Sep. 13, 2013.

*Primary Examiner* — Porfirio Nazario Gonzalez
(74) *Attorney, Agent, or Firm* — Nixon & Vanderhye P.C.

(57) ABSTRACT

For forming a thin ruthenium film of good quality by CVD method, it is necessary to form the thin film at low temperature. There hence is a desire for a ruthenium compound having a high reactivity to heat. This invention relates to a method of producing a ruthenium-containing film by CVD or the like using, as a raw material, a ruthenium complex mixture containing (2,4-dimethylpentadienyl)(ethyl-cyclopentadienyl) ruthenium and bis(2,4-dimethylpentadienyl)ruthenium, the amount of the latter compound being 0.1 to 100% by weight based on the weight of (2,4-dimethylpentadienyl)(ethylcyclopentadienyl)ruthenium, and the like.

8 Claims, 3 Drawing Sheets

RUTHENIUM COMPLEX MIXTURE, METHOD OF PRODUCING THE SAME, COMPOSITION FOR FILM FORMATION, RUTHENIUM-CONTAINING FILM, AND METHOD OF PRODUCING THE SAME

This application is the U.S. national phase of International Application No. PCT/JP2010/071208 filed 29 Nov. 2010 which designated the U.S. and claims priority to JP Patent Application Nos. 2009-297196 filed 28 Dec. 2009 and 2010-178697 filed 9 Aug. 2010, the entire contents of each of which are hereby incorporated by reference.

TECHNICAL FIELD

The present invention relates to a mixture of organometallic compounds which is useful, for example, in producing semiconductor elements, and to a method of producing the mixture, a composition for film formation, a metal-containing thin film, and a method of producing the film.

BACKGROUND ART

With the high integration of semiconductor memory elements, the miniaturization of memory cells is proceeding. Use of noble metals such as ruthenium, iridium, and platinum as electrode materials for such memory elements is being investigated. For use in DRAM elements among the memory elements, ruthenium is considered to be a promising electrode material because oxides thereof also have electrical conductivity and ruthenium has excellent suitability for microfabrication. An optimal process for producing a ruthenium-containing thin film in a highly integrated memory element is chemical vapor deposition (hereinafter referred to as CVD) because this method attains excellent step coverage. Organometallic compounds, which are easy to handle among metal compounds, are thought to be suitable for use as raw-material substances for forming thin films using the CVD or atomic layer deposition (hereinafter referred to as ALD). At present, an excellent organometallic compound for forming a thin ruthenium film or thin ruthenium oxide film is (2,4-dimethylpentadienyl)(ethylcyclopentadienyl)ruthenium (hereinafter referred to as DER) because this compound is liquid at ordinary temperature and has excellent handleability and renders stable feeding possible from the standpoints of stability and vapor pressure (patent document 1).

It is generally known that thin-film formation at a low temperature is advantageous to the formation of a thin ruthenium film of good quality by CVD, and there is a desire for a ruthenium compound that has high reactivity at lower temperatures than DER, which has been used hitherto. Non-patent document 1 has reported that bis(2,4-dimethylpentadienyl)ruthenium has high reactivity at lower temperatures than DER. However, since this complex has a melting point as high as 89° C., it is necessary that the complex should be fed after gasified through sublimation. The gasification through sublimation has a problem that not only the rate of carrier gas saturation is low, but also the raw-material gas concentration changes due to a change in the surface area of the solid, making it impossible to conduct stable feeding. A technique in which the complex is used as a solution in an organic solvent has been proposed as a measure for overcoming the problem (patent document 2). However, raw-material feeding by means of bubbling based on the technique has a problem that the solvent only volatilizes because of a difference in volatility between the solvent and the complex, resulting in precipitation of a solid. Consequently, this method is not considered to be an entirely stable method for raw-material feeding. Furthermore, since the dilution with a solvent results in a decrease in the concentration of the ruthenium complex as a raw material, the method brings about a decrease in the rate of film formation. The method hence is undesirable.

Meanwhile, it is known that the formation of a thin ruthenium film by CVD has another problem. That is, there is a delay time (incubation time) between initiation of the feeding of a raw material and initiation of thin-film formation on the substrate. A prolonged incubation time poses problems such as a decrease in the efficiency of thin-film production and difficulties in controlling film thickness. Although it has been reported that DER shows a shorter incubation time than raw materials which were investigated earlier (non-patent document 2), there still is an incubation time. There is a desire for a ruthenium compound which shows a shorter incubation time than DER.

PRIOR-ART DOCUMENTS

Patent Documents

Patent Document 1: JP-A-2003-342286
Patent Document 2: JP-A-5-132776
Patent Document 3: JP-A-2006-36780

Non-Patent Documents

Non-Patent Document 1: Kazuhisa Kawano et al., *Electrochemical and Solid-State Letters*, Vol. 10, Issue 6, pp. D60-D62 (2007)
Non-Patent Document 2: Tetsuo Shibutami et al., *Electrochemical and Solid-State Letters*, Vol. 6, Issue 9, pp. C117-C119 (2003)

SUMMARY OF THE INVENTION

Problems that the Invention is to Solve

For forming a thin ruthenium film of good quality by CVD, it is necessary to form the thin film at a low temperature. There hence is a desire for a ruthenium compound which is capable of foaming a thin film at lower temperatures than DER, which has been used hitherto. There also is a desire for a ruthenium compound which shows a shorter incubation time than DER. An object of the invention is to provide a ruthenium complex mixture which is capable of forming a thin film at lower temperatures than DER and which shows a shorter incubation time than DER, a method of producing the mixture, a composition for film formation, a ruthenium-containing thin film, and a method of producing the film.

Means for Solving the Problems

The present inventors diligently made investigations in order to overcome the problems. As a result, the inventors have found that by using a mixture of DER and bis(2,4-dimethylpentadienyl)ruthenium as a raw material, a ruthenium-containing film can be formed at a lower temperature than in the case where DER, which has been used hitherto, is used. Furthermore, the inventors have found that the ruthenium-containing film formed using the ruthenium complex mixture has better electrical properties than the ruthenium-containing film formed from DER. The invention has been thus completed.

Essential points of the invention reside in the following (1) to (10).

(1) A ruthenium complex mixture characterized by containing (2,4-dimethylpentadienyl)(ethylcyclopentadienyl)ruthenium and bis(2,4-dimethylpentadienyl)ruthenium, the amount of the latter compound being 0.1-100% by weight based on the (2,4-dimethylpentadienyl)(ethylcyclopentadienyl)ruthenium.

(2) The ruthenium complex mixture according to (1) which preferably is characterized in that the bis(2,4-dimethylpentadienyl)ruthenium is contained in an amount of 0.1-30% by weight based on the (2,4-dimethylpentadienyl)(ethylcyclopentadienyl)ruthenium.

(3) The ruthenium complex mixture according to (1) or (2) which preferably is characterized in that the bis(2,4-dimethylpentadienyl)ruthenium is contained in an amount of 0.1-15% by weight based on the (2,4-dimethylpentadienyl)(ethyl cyclopentadienyl)ruthenium.

(4) The ruthenium complex mixture according to any one of (1) to (3) which preferably is characterized by containing a compound that is analogous to (2,4-dimethylpentadienyl)(ethylcyclopentadienyl)ruthenium, the amount of the analogous compound being up to 5% by weight based on the (2,4-dimethylpentadienyl)(ethylcyclopentadienyl)ruthenium.

(5) A composition for forming a ruthenium-containing film, the composition being characterized by including the mixture according to any one of (1) to (4).

(6) A method of producing the ruthenium complex mixture according to any one of (1) to (4), the method being characterized by mixing (2,4-dimethylpentadienyl)(ethylcyclopentadienyl)ruthenium with bis(2,4-dimethylpentadienyl)ruthenium, the amount of the latter compound being 0.1-100% by weight based on the (2,4-dimethylpentadienyl)(ethylcyclopentadienyl)ruthenium.

(7) A method of producing the ruthenium complex mixture according to any one of (1) to (4), the method being characterized by subjecting bis(2,4-dimethylpentadienyl)ruthenium to reaction with ethylcyclopentadiene in the presence of zinc and a solvent, the amount of the ethylcyclopentadiene being 0.5-1.0 mol per mole of the bis(2,4-dimethylpentadienyl)ruthenium.

(8) The method of producing a ruthenium complex mixture according to (7), wherein the bis(2,4-dimethylpentadienyl) ruthenium preferably is bis(2,4-dimethylpentadienyl)ruthenium obtained by subjecting 2,4-dimethyl-1,3-pentadiene to reaction with halogenated ruthenium represented by general formula [1]

$$RuX_3 \cdot nH_2O \quad [1]$$

[wherein X represents a halogen atom and n indicates 0-10] in the presence of a solvent and zinc.

(9) A method of producing a ruthenium-containing film, the method being characterized by using the ruthenium complex mixture according to any one of (1) to (4) as a raw material.

(10) A ruthenium-containing film characterized by being produced by the method according to (9).

Namely, the invention provides a ruthenium complex mixture characterized by containing DER and bis(2,4-dimethylpentadienyl)ruthenium, the amount of the latter compound being 0.1-100% by weight based on the DER. The invention further provides a composition for forming a ruthenium-containing film, the composition being characterized by including the ruthenium complex mixture. The invention furthermore provides a method of producing the ruthenium complex mixture, the method being characterized by mixing DER with bis(2,4-dimethylpentadienyl)ruthenium, the amount of the latter compound being 0.1-100% by weight based on the DER. The invention still further provides a method of producing the ruthenium complex mixture, the method being characterized by subjecting bis(2,4-dimethylpentadienyl)ruthenium to reaction with ethylcyclopentadiene in the presence of zinc and a solvent, the amount of the ethylcyclopentadiene being 0.5-1.0 mol per mole of the bis(2,4-dimethylpentadienyl)ruthenium. The invention still further provides a method of producing a ruthenium-containing film, the method being characterized by using the ruthenium complex mixture as a raw material. The invention still further provides a ruthenium-containing film characterized by being produced by the method.

Effects of the Invention

The ruthenium complex mixture according to the invention can be used as a composition for forming a ruthenium-containing film. Use of the mixture as a raw material for film formation renders stable feeding of the raw material possible and enables a ruthenium-containing film to be produced at a lower temperature than in the case where DER is used as a raw material. The ruthenium-containing film obtained has better electrical properties than the ruthenium-containing film produced from DER.

Furthermore, it is possible to produce a ruthenium-containing film in a shorter period than in the case where DER is used as a raw material.

MODES FOR CARRYING OUT THE INVENTION

The invention will be explained below in detail.

The ruthenium complex mixture according to the invention contains DER and bis(2,4-dimethylpentadienyl)ruthenium, the amount of which is 0.1-100% by weight based on the DER, as stated above. The mixture may contain these two components as the only ruthenium complexes, or may contain other ruthenium complexes. Examples of the other ruthenium complexes include DER analogue compounds. The DER analogue compounds are bisdienylruthenium compounds other than DER and bis(2,4-dimethylpentadienyl)ruthenium, and examples thereof include bis(ethylcyclopentadienyl)ruthenium, (1,3-dimethylcyclopentadienyl)(ethylcyclopentadienyl)ruthenium, bis(1,3-dimethylcyclopentadienyl)ruthenium, and (1,3-dimethylcyclopentadienyl)(2,4-dimethylpentadienyl)ruthenium. The content thereof is not particularly limited. And, since the mixture is intended to be used as a raw material for producing a ruthenium-containing film, it is preferred that the content of the DER analogue compounds should be in such a range that these compounds do not adversely affect the film formation. Specifically, in the case of the ruthenium complexes shown above, i.e., bis(ethylcyclopentadienyl)ruthenium, (1,3-dimethylcyclopentadienyl)(ethylcyclopentadienyl)ruthenium, bis(1,3-dimethylcyclopentadienyl)ruthenium, and the like, it is preferred that the total content thereof should be up to 5% by weight based on the DER. Meanwhile, in the case of ruthenium complexes which do not adversely affect film formation, these ruthenium complexes may be contained in an amount of about 5% by weight or more. Examples of the ruthenium complexes which do not adversely affect film formation include (1,3-dimethylcyclopentadienyl)(2,4-dimethylpentadienyl)ruthenium, and should not be construed as being limited to this ruthenium complex.

The ruthenium complex mixture of the invention may contain a solvent, a stabilizer, etc.

The ruthenium complex mixture may be in an even solution state, or may be in a state in which a solid formed by partial precipitation of the DER and/or bis(2,4-dimethylpentadienyl)ruthenium coexists. In the case where the solid coexists, the mixture can be heated so that the mixture is used as an even solution. Alternatively, the mixture may be diluted with an adequate solvent to obtain an even solution.

The content of the bis(2,4-dimethylpentadienyl)ruthenium is 0.1-100% by weight based on the DER. In the case where the content thereof is less than 0.1% by weight, use of this mixture as a raw material for film formation at a low temperature results in a decrease in the amount of nuclei which generate in the initial stage in the film formation, making it impossible to obtain the effect of rendering low-temperature film formation possible. On the other hand, in the case where the content thereof exceeds 100% by weight, this mixture must be held at 80° C. or higher in order to keep the mixture in an even solution state when the mixture is used as a raw material for film formation. As a result, the bis(2,4-dimethylpentadienyl)ruthenium suffers considerable thermal decomposition. When the thermal decomposition of the bis(2,4-dimethylpentadienyl)ruthenium is taken into account, it is preferred that the mixture should contain bis(2,4-dimethylpentadienyl)ruthenium in an amount of 0.1-30% by weight based on the DER. Furthermore, the mixture which contains bis(2,4-dimethylpentadienyl)ruthenium in an amount of 0.1-15% by weight based on the DER is preferred from the standpoint of handleability because this mixture is an even solution at room temperature. The mixture which contains bis(2,4-dimethylpentadienyl)ruthenium in an amount of 1-15% by weight based on the DER is more preferred from the standpoint of the effect of shortening incubation time.

The ruthenium complex mixture of the invention can be produced by directly mixing DER with 0.1-100% by weight, preferably 0.1-30% by weight, more preferably 0.1-15% by weight, bis(2,4-dimethylpentadienyl)ruthenium based on the DER (production method 1).

It is essential that the temperature at which DER is mixed with bis(2,4-dimethylpentadienyl)ruthenium should be lower than 210° C. because bis(2,4-dimethylpentadienyl)ruthenium has a decomposition temperature of 210° C. Since bis(2,4-dimethylpentadienyl)ruthenium has a melting point of 89° C., DER and bis(2,4-dimethylpentadienyl)ruthenium intermingle with each other in any proportion at 89° C. or higher. It is, however, preferred that the two ingredients should be mixed at 80° C. or lower because the bis(2,4-dimethylpentadienyl)ruthenium suffers considerable thermal decomposition at such higher temperatures.

An adequate solvent may be cause to coexist during the mixing. Thus, the ruthenium complex mixture of the invention can be produced as an even solution without requiring heating, and the DER and/or the bis(2,4-dimethylpentadienyl)ruthenium can be inhibited from being thermally decomposed.

Examples of the solvent to be used here include alcohols such as methanol, ethanol, propanol, and isopropanol, esters such as ethyl acetate, butyl acetate, and isoamyl acetate, glycol ethers such as ethylene glycol monoethyl ether, ethylene glycol monomethyl ether, and ethylene glycol monobutyl ether, ethers such as diethyl ether, t-butyl methyl ether, glyme, diglyme, triglyme, and tetrahydrofuran, ketones such as t-butyl methyl ketone, isobutyl methyl ketone, ethyl butyl ketone, dipropyl ketone, diisobutyl ketone, methyl amyl ketone, cyclohexanone, and acetone, and hydrocarbons such as hexane, cyclohexane, ethylcyclohexane, heptane, octane, benzene, toluene, and xylene. And, the solvent is not particularly limited.

The DER and the bis(2,4-dimethylpentadienyl)ruthenium can be produced by the method described in patent document 1 and the method described in patent document 3, respectively.

The ruthenium complex mixture of the invention can be obtained by subjecting bis(2,4-dimethylpentadienyl)ruthenium to reaction with ethylcyclopentadiene in the presence of zinc and a solvent (production method 2). The reaction temperature in this method is preferably −20 to 100° C., more preferably −20 to 80° C.

When bis(2,4-dimethylpentadienyl)ruthenium and ethylcyclopentadiene are subjected to reaction with each other, the ethylcyclopentadiene is subjected to reaction in an amount of 0.5-1.0 mol per mole of the bis(2,4-dimethylpentadienyl)ruthenium. The reasons for this are as follows. In the case where the amount of the ethylcyclopentadiene is less than 0.5 mol, the bis(2,4-dimethylpentadienyl)ruthenium remains unreacted in a larger amount. In the case where ethylcyclopentadiene is used in an amount exceeding 1.0 mol, bis(ethylcyclopentadienyl)ruthenium is yielded as a by-product.

The amount of the zinc to be used in this method is not particularly limited. And, the amount thereof per mole of the bis(2,4-dimethylpentadienyl)ruthenium is preferably 1.0 mol or more, more preferably 1.5 mol or more. Even when zinc is used in large excess, this method is disadvantageous from the standpoint of profitability. It is therefore advantageous to use zinc in an amount of 1.5-100 mol.

The reaction solvent for use in this method is not particularly limited. And, it is preferred to use an alcohol as part or the whole of the solvent. In the case where methanol, in particular, is used among alcohols, the following procedure may be employed. After completion of the reaction, the reaction mixture is filtered to remove the excess zinc, and bis(2,4-dimethylpentadienyl)ruthenium and DER are thereafter extracted with a solvent which does not freely intermingle with methanol. The extract is concentrated, and the resultant oily matter or suspension is purified. Thus, the desired compounds can be obtained through industrially advantageous steps. Examples of the solvent which does not freely intermingle with methanol include aliphatic hydrocarbons such as pentane, hexane, heptane, and octane. Pentane and hexane are especially preferred of these because the two solvents are available at low cost and are industrially advantageous.

Methods for recovering and purifying the products are not particularly limited. And, use can be made of distillation and column chromatography. Examples of carriers for the column chromatography include porous polymers, such as divinylbenzene copolymers and styrene/divinylbenzene copolymers, and alumina, but the carriers are not limited to these examples. When these fillers are to be used, one filler may be used alone or a mixture of two or more fillers may be used. Examples of eluents include alcohols such as methanol, ethanol, and isopropanol, esters such as ethyl acetate and butyl acetate, halogenated hydrocarbons such as dichloromethane, chloroform, and carbon tetrachloride, and hydrocarbons such as pentane, hexane, cyclohexane, methylcyclohexane, ethylcyclohexane, heptane, octane, toluene, and xylene. When these separation solvents are to be used, one separation solvent may be used alone or a mixture of two or more solvents which intermingle with each other may be used. Preferred of those separation solvents, from the standpoint of the polarity thereof, are hydrocarbons such as pentane, hexane, heptane, octane, and cyclohexane. From the standpoint of production cost, hexane is most preferred.

The bis(2,4-dimethylpentadienyl)ruthenium to be subjected to the reaction can be obtained by subjecting 2,4-dimethyl-1,3-pentadiene to reaction with halogenated ruthenium represented by the general formula [1]

$$RuX_3 \cdot nH_2O \qquad [1]$$

[wherein X represents a halogen atom and n indicates 0-10] in the presence of a solvent and zinc.

In the general formula [1], X represents a halogen atom. Examples of the halogen include fluorine, chlorine, bromine, or iodine. The halogen preferably is bromine or chlorine. n in the general formula [1] indicates 0-10, and the general formula [1] in which n=0 represents an anhydride. When n is not 0, the general formula [1] represents a hydrate.

The amount of the zinc to be used in the reaction is not particularly limited. And, the amount thereof per mole of the halogenated ruthenium represented by the general formula [1] is preferably 1.0 mol or more, more preferably 1.5 mol or more. Even when zinc is used in large excess, this method is disadvantageous from the standpoint of profitability. It is therefore advantageous to use zinc in an amount of 1.5-100 mol.

When 2,4-dimethyl-1,3-pentadiene is to be subjected to reaction with halogenated ruthenium represented by the general formula [1], it is preferred that the 2,4-dimethyl-1,3-pentadiene should be used and subjected to reaction in an amount of 2 mol or more per mole of the general formula [1]. Even when 2,4-dimethyl-1,3-pentadiene is used in large excess, this method is disadvantageous from the standpoint of profitability. It is therefore advantageous to use the compound in an amount of 2-20 mol.

When 2,4-dimethyl-1,3-pentadiene is subjected to reaction with halogenated ruthenium represented by the general formula [1], it is preferred to subject the reactants to reaction at a temperature of −20 to 100° C., more preferably −20 to 80° C.

In the case where 2,4-dimethyl-1,3-pentadiene is subjected to reaction with halogenated ruthenium represented by the general formula [1] to produce bis(2,4-dimethylpentadienyl)ruthenium in the invention, the bis(2,4-dimethylpentadienyl)ruthenium obtained may be directly subjected to reaction with ethylcyclopentadiene within the pot without being isolated. Thus, a bis(2,4-dimethylpentadienyl)ruthenium/DER mixture of the invention can be produced.

It is preferred that the operation in production method 1 and the reaction in production method 2, in the invention, should be conducted in a nitrogen or inert gas atmosphere. Examples of the inert gas include helium, neon, argon, krypton, xenon, and radon. Nitrogen and argon are more preferred of these because nitrogen and argon are available at low cost and are industrially advantageous.

A ruthenium-containing film can be produced using the ruthenium complex mixture of the invention as a raw material. Techniques for producing a ruthenium-containing film are not particularly limited. Examples thereof include CVD, ALD, spin coating, dip coating, and spraying. In the case where a ruthenium-containing film is to be produced on a substrate by CVD or ALD using the ruthenium complex mixture of the invention as a raw material, the ruthenium complex mixture is gasified and fed to the substrate.

Methods for feeding the raw material to a film deposition chamber for CVD or ALD are not particularly limited, and examples thereof include bubbling and a liquid vaporization/feeding system. However, when bubbling into the solution is used over a long period, it is difficult to keep the composition of the raw material constant because of a difference in vapor pressure between the bis(2,4-dimethylpentadienyl)ruthenium and the DER. Consequently, it is preferred to vaporize and feed the raw material by means of a liquid vaporization/feeding system.

The carrier gas to be used in film formation by ALD or CVD preferably is a rare gas or nitrogen. Preferred for reasons of profitability are nitrogen, helium, neon, and argon.

Examples of reactant gases for the film formation by ALD or CVD include hydrogen, oxygen, laughing gas, ammonia, hydrogen chloride, nitric acid gas, formic acid, and acetic acid. The raw material can be decomposed with the aid of heat only. And, light, a plasma, or the like may be used in combination with heat.

According to the invention, the following ruthenium-containing films, for example, are obtained. In the case where the ruthenium complex mixture of the invention is used alone, a metallic-ruthenium film, a ruthenium oxide film, or the like is obtained. In the case where the ruthenium complex mixture is used in combination with another metal source, a ruthenium-containing composite film is obtained. For example, when the ruthenium complex mixture is used in combination with a strontium source, an $SrRuO_3$ film is obtained. And, strontium-containing films which can be obtained in this case are not limited to that example. Examples of the strontium source include bis(dipivaloylmethanato)strontium, diethoxystrontium, and bis(1,1,1,5,5,5-hexafluoro-2,4-pentanedionato) strontium. And, the strontium source is not limited to these examples. In the case where the ruthenium complex mixture is used in combination with another metal source, the raw materials may be separately fed or may be mixed together and then fed.

EXAMPLES

Specific embodiments to which the invention has been applied are explained below by reference to Examples. The invention should not be construed as being limited to the following Examples.

Example 1

A 10.0 g portion of DER was weighed out in a Schlenk tube in which the atmosphere had been replaced with argon, and 0.1 g (1% by weight based on the DER) of bis(2,4-dimethylpentadienyl)ruthenium was added thereto. The contents were stirred at 27° C. for 60 minutes to obtain 10.1 g of an even yellow solution. The composition of this solution was ascertained by gas chromatography. As a result, this solution was found to include DER and bis(2,4-dimethylpentadienyl)ruthenium, the amount of which was 1% by weight based on the DER.

Example 2

A 10.0 g portion of DER was weighed out in a Schlenk tube in which the atmosphere had been replaced with argon, and 0.5 g (5% by weight based on the DER) of bis(2,4-dimethylpentadienyl)ruthenium was added thereto. The contents were stirred at 27° C. for 60 minutes to obtain 10.5 g of an even yellow solution. The composition of this solution was ascertained by gas chromatography. As a result, this solution was found to include DER and bis(2,4-dimethylpentadienyl)ruthenium, the amount of which was 5% by weight based on the DER.

Example 3

A 10.0 g portion of DER was weighed out in a Schlenk tube in which the atmosphere had been replaced with argon, and 1.5 g (15% by weight based on the DER) of bis(2,4-dimethylpentadienyl)ruthenium was added thereto. The contents were stirred at 27° C. for 60 minutes to obtain 11.5 g of an even yellow solution. The composition of this solution was ascertained by gas chromatography. As a result, this solution was found to include DER and bis(2,4-dimethylpentadienyl)ruthenium, the amount of which was 15% by weight based on the DER.

Example 4

A 1.0 g portion of DER was weighed out in a Schlenk tube in which the atmosphere had been replaced with argon, and 1.0 g (100% by weight based on the DER) of bis(2,4-dimethylpentadienyl)ruthenium was added thereto. The contents were stirred at 80° C. for 60 minutes to obtain 2.0 g of an even yellow solution. The composition of this solution was ascertained by gas chromatography. As a result, this solution was found to include DER and bis(2,4-dimethylpentadienyl)ruthenium, the amount of which was 100% by weight based on the DER.

Example 5

A 10.0 g portion of DER was weighed out in a Schlenk tube in which the atmosphere had been replaced with argon, and 1.5 g (15% by weight based on the DER) of bis(2,4-dimethylpentadienyl)ruthenium and 0.4 g (4.0% by weight based on the DER) of bis(ethylcyclopentadienyl)ruthenium were added thereto. The contents were stirred at 27° C. for 60 minutes to obtain 11.9 g of an even yellow solution. The composition of this solution was ascertained by gas chromatography. As a result, this solution was found to include DER, bis(2,4-dimethylpentadienyl)ruthenium, the amount of which was 15% by weight based on the DER, and bis(ethylcyclopentadienyl)ruthenium, the amount of which was 4.0% by weight based on the DER.

Example 6

A 10.0 g portion of DER was weighed out in a Schlenk tube in which the atmosphere had been replaced with argon, and 1.5 g (15% by weight based on the DER) of bis(2,4-dimethylpentadienyl)ruthenium and 0.4 g (4.0% by weight based on the DER) of (1,3-dimethylcyclopentadienyl)(ethylcyclopentadienyl)ruthenium were added thereto. The contents were stirred at 27° C. for 60 minutes to obtain 11.9 g of an even yellow solution. The composition of this solution was ascertained by gas chromatography. As a result, this solution was found to include DER, bis(2,4-dimethylpentadienyl)ruthenium, the amount of which was 15% by weight based on the DER, and (1,3-dimethylcyclopentadienyl)(ethylcyclopentadienyl)ruthenium, the amount of which was 4.0% by weight based on the DER.

Example 7

A 10.0 g portion of DER was weighed out in a Schlenk tube in which the atmosphere had been replaced with argon, and 1.5 g (15% by weight based on the DER) of bis(2,4-dimethylpentadienyl)ruthenium and 0.4 g (4.0% by weight based on the DER) of bis(1,3-dimethylcyclopentadienyl)ruthenium were added thereto. The contents were stirred at 27° C. for 60 minutes to obtain 11.9 g of an even yellow solution. The composition of this solution was ascertained by gas chromatography. As a result, this solution was found to include DER, bis(2,4-dimethylpentadienyl)ruthenium, the amount of which was 15% by weight based on the DER, and bis(1,3-dimethylcyclopentadienyl)ruthenium, the amount of which was 4.0% by weight based on the DER.

Example 8

A 10.0 g portion of DER was weighed out in a Schlenk tube in which the atmosphere had been replaced with argon, and 1.5 g (15% by weight based on the DER) of bis(2,4-dimethylpentadienyl)ruthenium, 0.2 g (2.0% by weight based on the DER) of bis(ethylcyclopentadienyl)ruthenium, and 0.2 g (2.0% by weight based on the DER) of (1,3-dimethylcyclopentadienyl)(ethylcyclopentadienyl)ruthenium were added thereto. The contents were stirred at 27° C. for 60 minutes to obtain 11.9 g of an even yellow solution. The composition of this solution was ascertained by gas chromatography. As a result, this solution was found to include DER, bis(2,4-dimethylpentadienyl)ruthenium, the amount of which was 15% by weight based on the DER, bis(ethylcyclopentadienyl)ruthenium, the amount of which was 2.0% by weight based on the DER, and (1,3-dimethylcyclopentadienyl)(ethylcyclopentadienyl)ruthenium, the amount of which was 2.0% by weight based on the DER.

Example 9

A 10.0 g portion of DER was weighed out in a Schlenk tube in which the atmosphere had been replaced with argon, and 1.5 g (15% by weight based on the DER) of bis(2,4-dimethylpentadienyl)ruthenium, 0.2 g (2.0% by weight based on the DER) of bis(ethylcyclopentadienyl)ruthenium, and 0.2 g (2.0% by weight based on the DER) of bis(1,3-dimethylcyclopentadienyl)ruthenium were added thereto. The contents were stirred at 27° C. for 60 minutes to obtain 11.9 g of an even yellow solution. The composition of this solution was ascertained by gas chromatography. As a result, this solution was found to include DER, bis(2,4-dimethylpentadienyl)ruthenium, the amount of which was 15% by weight based on the DER, bis(ethylcyclopentadienyl)ruthenium, the amount of which was 2.0% by weight based on the DER, and bis(1,3-dimethylcyclopentadienyl)ruthenium, the amount of which was 2.0% by weight based on the DER.

Example 10

A 10.0 g portion of DER was weighed out in a Schlenk tube in which the atmosphere had been replaced with argon, and 1.5 g (15% by weight based on the DER) of bis(2,4-dimethylpentadienyl)ruthenium, 0.2 g (2.0% by weight based on the DER) of (1,3-dimethylcyclopentadienyl)(ethylcyclopentadienyl)ruthenium, and 0.2 g (2.0% by weight based on the DER) of bis(1,3-dimethylcyclopentadienyl)ruthenium were added thereto. The contents were stirred at 27° C. for 60 minutes to obtain 11.9 g of an even yellow solution. The composition of this solution was ascertained by gas chromatography. As a result, this solution was found to include DER, bis(2,4-dimethylpentadienyl)ruthenium, the amount of which was 15% by weight based on the DER, (1,3-dimethylcyclopentadienyl)(ethylcyclopentadienyl)ruthenium, the amount of which was 2.0% by weight based on the DER, and bis(1,3-dimethylcyclopentadienyl)ruthenium, the amount of which was 2.0% by weight based on the DER.

Example 11

A 10.0 g portion of DER was weighed out in a Schlenk tube in which the atmosphere had been replaced with argon, and 1.5 g (15% by weight based on the DER) of bis(2,4-dimethylpentadienyl)ruthenium, 0.1 g (1.0% by weight based on the DER) of bis(ethylcyclopentadienyl)ruthenium, 0.1 g (1.0% by weight based on the DER) of (1,3-dimethylcyclopentadienyl)(ethylcyclopentadienyl)ruthenium, and 0.1 g (1.0% by weight based on the DER) of bis(1,3-dimethylcyclopentadienyl)ruthenium were added thereto. The contents were stirred at 27° C. for 60 minutes to obtain 11.8 g of an even yellow solution. The composition of this solution was ascertained by gas chromatography. As a result, this solution was found to include DER, bis(2,4-dimethylpentadienyl)ruthenium, the amount of which was 15% by weight based on the DER, bis(ethylcyclopentadienyl)ruthenium, the amount of which was 1.0% by weight based on the DER, (1,3-dimethylcyclopentadienyl)(ethylcyclopentadienyl)ruthenium, the amount of which was 1.0% by weight based on the DER, and bis(1, 3-dimethylcyclopentadienyl)ruthenium, the amount of which was 1.0% by weight based on the DER.

Example 12

A 1.36 g portion of zinc was weighed out in a three-necked flask, and the atmosphere in the vessel was replaced with argon. Thereto were added 4.32 g of 2,4-dimethyl-1,3-pentadiene and 12 mL of methanol to obtain a suspension. A solution obtained by dissolving 2.52 g of ruthenium trichloride n-hydrate (n=about 3) in 40 mL of methanol was added dropwise to the suspension over 40 minutes with cooling with ice. After completion of the dropwise addition, the resultant mixture was stirred for 120 minutes with cooling with ice. Thereafter, the mixture was heated to 60° C. and stirred for 1 hour. This mixture was temporarily allowed to cool, and 0.96 g of ethylcyclopentadiene was added thereto. The resultant mixture was immediately stirred at room temperature for 1 hour and then stirred at an elevated temperature of 60° C. for 30 minutes. After completion of the reaction, the reaction mixture was cooled to room temperature, and the unreacted zinc was removed therefrom with a glass filter. Thereafter, the mixture was extracted with 30 mL of hexane once and 20 mL of hexane four times. The extract was concentrated at a reduced pressure, and the resultant oily matter was subjected to vacuum distillation to obtain, as a desired product, 2.18 g of a mixture of DER and bis(2,4-dimethylpentadienyl)ruthenium. The composition of this mixture was ascertained by gas chromatography. As a result, the mixture was found to have a content of bis(2,4-dimethylpentadienyl)ruthenium of 14% by weight based on the DER, and the yield was 69.5%.

Example 13

A 1.36 g portion of zinc was weighed out in a three-necked flask, and the atmosphere in the vessel was replaced with argon. Thereto were added 4.32 g of 2,4-dimethyl-1,3-pentadiene and 12 mL of methanol to obtain a suspension. A solution obtained by dissolving 2.53 g of ruthenium trichloride n-hydrate (n=about 3) in 40 mL of methanol was added dropwise to the suspension over 40 minutes with cooling with ice. After completion of the dropwise addition, the resultant mixture was stirred for 120 minutes with cooling with ice. Thereafter, the mixture was heated to 60° C. and stirred for 1 hour. This mixture was temporarily allowed to cool, and 0.52 g of ethylcyclopentadiene was added thereto. The resultant mixture was immediately stirred at room temperature for 1 hour and then stirred at an elevated temperature of 60° C. for 30 minutes. After completion of the reaction, the reaction mixture was cooled to room temperature, and the unreacted zinc was removed therefrom with a glass filter. Thereafter, the mixture was extracted with 30 mL of hexane once and 20 mL of hexane four times. The extract was concentrated at a reduced pressure, and the resultant suspension was subjected to column chromatography using alumina as a column packing and hexane as an eluent. Thus, 2.98 g of a mixture of DER and bis(2,4-dimethylpentadienyl)ruthenium was obtained as a desired product. The composition of this mixture was ascertained by gas chromatography. As a result, the mixture was found to have a content of bis(2,4-dimethylpentadienyl)ruthenium of 98% by weight based on the DER, and the yield was 82.5%.

Example 14

Figure 1:
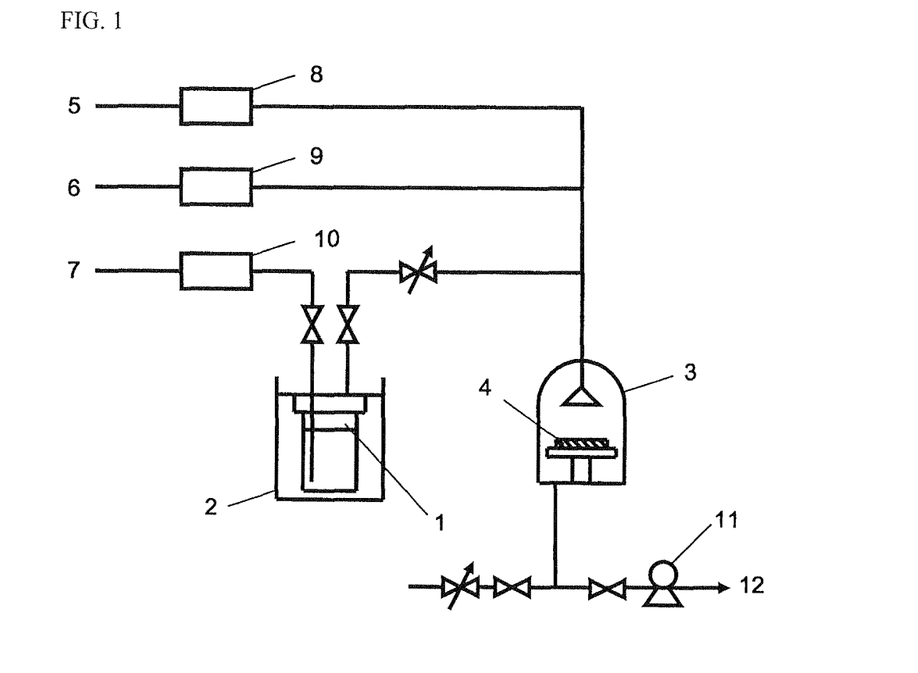
FIG. 1 is a view showing the CVD apparatus used in Examples 14 to 23, 28 and in Comparative Examples 1, 3, 4.

The ruthenium complex mixture produced by the method described in Example 1 (which included DER and bis(2,4-dimethylpentadienyl)ruthenium, the amount of which was 1% by weight based on the DER) was used as a raw material to conduct film deposition on an $SiO_2/Si$ substrate for 1 hour by CVD using the apparatus of FIG. 1 under the conditions of a raw-material temperature of 66° C., a carrier gas (Ar) flow rate of 30 sccm, a raw-material pressure of 150 Ton, a diluent gas (Ar) flow rate of 169 sccm, a reactant gas ($O_2$) flow rate of 0.16 sccm, a substrate temperature of 240° C., and a reaction-chamber internal pressure of 10 Torr. The thin film produced was examined by fluorescent X-ray spectroscopy. As a result, a characteristic X-ray line assigned to ruthenium was observed. The film was examined for thickness with a scanning electron microscope (hereinafter referred to as SEM) and, as a result, the thickness thereof was found to be 20 nm.

Example 15

The ruthenium complex mixture produced by the method described in Example 2 (which included DER and bis(2,4-dimethylpentadienyl)ruthenium, the amount of which was 5% by weight based on the DER) was used as a raw material to conduct film deposition using the apparatus of FIG. 1 under the same conditions as in Example 14. The thin film produced was examined by fluorescent X-ray spectroscopy.

As a result, a characteristic X-ray line assigned to ruthenium was observed. The film was examined for thickness with an SEM and, as a result, the thickness thereof was found to be 25 nm.

Example 16

The ruthenium complex mixture produced by the method described in Example 3 (which included DER and bis(2,4-dimethylpentadienyl)ruthenium, the amount of which was 15% by weight based on the DER) was used as a raw material to conduct film deposition using the apparatus of FIG. 1 under the same conditions as in Example 14. The thin film produced was examined by fluorescent X-ray spectroscopy.

As a result, a characteristic X-ray line assigned to ruthenium was observed. The film was examined for thickness with an SEM and, as a result, the thickness thereof was found to be 30 nm.

Example 17

The ruthenium complex mixture produced by the method described in Example 5 (which included DER, bis(2,4-dimethylpentadienyl)ruthenium, the amount of which was 15% by weight based on the DER, and bis(ethylcyclopentadienyl)ruthenium, the amount of which was 4.0% by weight based on the DER) was used as a raw material to conduct film deposition using the apparatus of FIG. 1 under the same conditions as in Example 14. The thin film produced was examined by fluorescent X-ray spectroscopy. As a result, a characteristic X-ray line assigned to ruthenium was observed. The film was examined for thickness with an SEM and, as a result, the thickness thereof was found to be 25 nm.

Example 18

The ruthenium complex mixture produced by the method described in Example 6 (which included DER, bis(2,4-dimethylpentadienyl)ruthenium, the amount of which was 15% by weight based on the DER, and (1,3-dimethylcyclopentadienyl)(ethylcyclopentadienyl)ruthenium, the amount of which was 4.0% by weight based on the DER) was used as a raw material to conduct film deposition using the apparatus of FIG. 1 under the same conditions as in Example 14. The thin film produced was examined by fluorescent X-ray spectroscopy. As a result, a characteristic X-ray line assigned to ruthenium was observed. The film was examined for thickness with an SEM and, as a result, the thickness thereof was found to be 25 nm.

Example 19

The ruthenium complex mixture produced by the method described in Example 7 (which included DER, bis(2,4-dimethylpentadienyl)ruthenium, the amount of which was 15% by weight based on the DER, and bis(1,3-dimethylcyclopentadienyl)ruthenium, the amount of which was 4.0% by weight based on the DER) was used as a raw material to conduct film deposition using the apparatus of FIG. 1 under the same conditions as in Example 14. The thin film produced was examined by fluorescent X-ray spectroscopy. As a result, a characteristic X-ray line assigned to ruthenium was observed. The film was examined for thickness with an SEM and, as a result, the thickness thereof was found to be 25 nm.

Example 20

The ruthenium complex mixture produced by the method described in Example 8 (which included DER, bis(2,4-dimethylpentadienyl)ruthenium, the amount of which was 15% by weight based on the DER, bis(ethylcyclopentadienyl)ruthenium, the amount of which was 2.0% by weight based on the DER, and (1,3-dimethylcyclopentadienyl)(ethylcyclopentadienyl)ruthenium, the amount of which was 2.0% by weight based on the DER) was used as a raw material to conduct film deposition using the apparatus of FIG. 1 under the same conditions as in Example 14. The thin film produced was examined by fluorescent X-ray spectroscopy. As a result, a characteristic X-ray line assigned to ruthenium was observed. The film was examined for thickness with an SEM and, as a result, the thickness thereof was found to be 25 nm.

Example 21

The ruthenium complex mixture produced by the method described in Example 9 (which included DER, bis(2,4-dimethylpentadienyl)ruthenium, the amount of which was 15% by weight based on the DER, bis(ethylcyclopentadienyl)ruthenium, the amount of which was 2.0% by weight based on the DER, and bis(1,3-dimethylcyclopentadienyl)ruthenium, the amount of which was 2.0% by weight based on the DER) was used as a raw material to conduct film deposition using the apparatus of FIG. 1 under the same conditions as in Example 14. The thin film produced was examined by fluorescent X-ray spectroscopy. As a result, a characteristic X-ray line assigned to ruthenium was observed. The film was examined for thickness with an SEM and, as a result, the thickness thereof was found to be 25 nm.

Example 22

The ruthenium complex mixture produced by the method described in Example 10 (which included DER, bis(2,4-dimethylpentadienyl)ruthenium, the amount of which was 15% by weight based on the DER, (1,3-dimethylcyclopentadienyl)(ethylcyclopentadienyl)ruthenium, the amount of which was 2.0% by weight based on the DER, and bis(1,3-dimethylcyclopentadienyl)ruthenium, the amount of which was 2.0% by weight based on the DER) was used as a raw material to conduct film deposition using the apparatus of FIG. 1 under the same conditions as in Example 14. The thin film produced was examined by fluorescent X-ray spectroscopy.

As a result, a characteristic X-ray line assigned to ruthenium was observed. The film was examined for thickness with an SEM and, as a result, the thickness thereof was found to be 25 nm.

Example 23

The ruthenium complex mixture produced by the method described in Example 11 (which included DER, bis(2,4-dimethylpentadienyl)ruthenium, the amount of which was 15% by weight based on the DER, bis(ethylcyclopentadienyl)ruthenium, the amount of which was 1.0% by weight based on the DER, (1,3-dimethylcyclopentadienyl)(ethylcyclopentadienyl)ruthenium, the amount of which was 1.0% by weight based on the DER, and bis(1,3-dimethylcyclopentadienyl)ruthenium, the amount of which was 1.0% by weight based on the DER) was used as a raw material to conduct film deposition using the apparatus of FIG. 1 under the same conditions as in Example 14. The thin film produced was examined by fluorescent X-ray spectroscopy.

As a result, a characteristic X-ray line assigned to ruthenium was observed. The film was examined for thickness with an SEM and, as a result, the thickness thereof was found to be 27 nm.

Example 24

Figure 2:
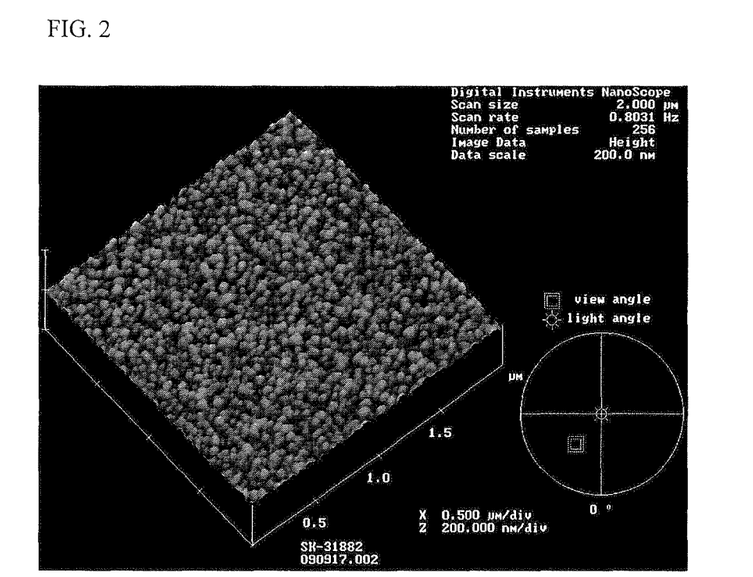
FIG. 2 is a view showing an image obtained with an atomic force microscope (hereinafter referred to as AFM image) in Example 24.

The ruthenium-containing film produced by the method described in Example 14 was examined for electrical properties by the four-probe method. As a result, the film was found to have a resistivity of 260 $\mu\Omega\cdot$cm. The surface smoothness of the film was evaluated with an AFM (FIG. 2). As a result, the film was found to have an arithmetic mean roughness of 6 nm.

Example 25

Figure 3:
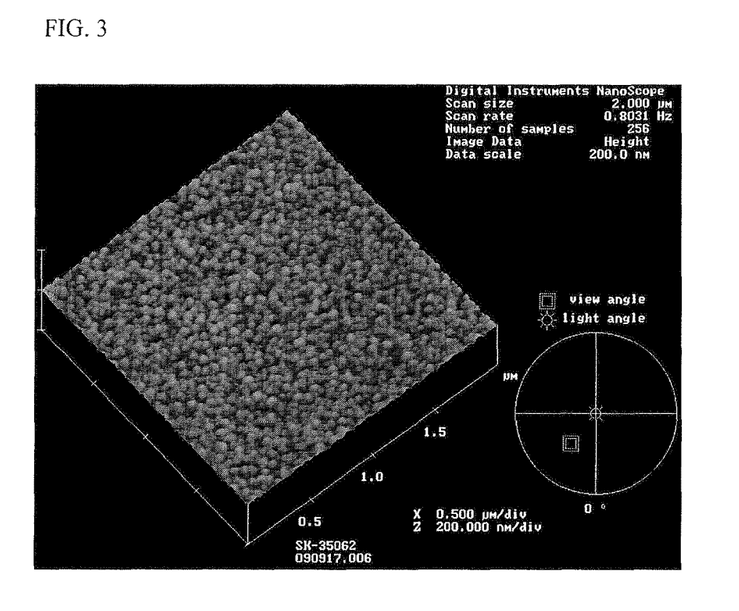
FIG. 3 is a view showing an AFM image of the film obtained in Example 25.

The ruthenium-containing film produced by the method described in Example 15 was examined for electrical properties by the four-probe method. As a result, the film was found to have a resistivity of 60 $\mu\Omega\cdot$cm. The surface smoothness of the film was evaluated with an AFM (FIG. 3). As a result, the film was found to have an arithmetic mean roughness of 4 nm.

Example 26

Figure 4:
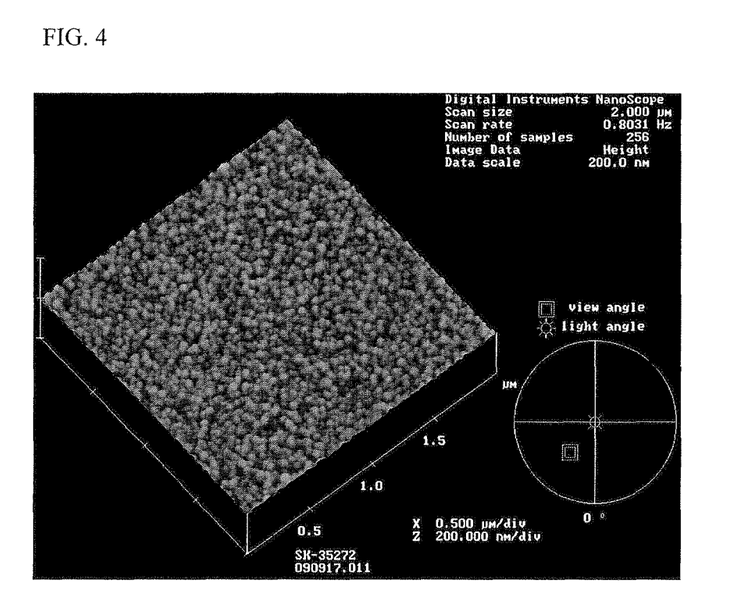
FIG. 4 is a view showing an AFM image of the film obtained in Example 26.

The ruthenium-containing film produced by the method described in Example 16 was examined for electrical properties by the four-probe method. As a result, the film was found to have a resistivity of 50 μΩ·cm. The surface smoothness of the film was evaluated with an AFM (FIG. 4). As a result, the film was found to have an arithmetic mean roughness of 3 nm.

Example 27

The ruthenium-containing film produced by the method described in Example 23 was examined for electrical properties by the four-probe method. As a result, the film was found to have a resistivity of 55 μΩ·cm.

Example 28

The ruthenium complex mixture produced by the method described in Example 11 (which included DER, bis(2,4-dimethylpentadienyl)ruthenium, the amount of which was 15% by weight based on the DER, bis(ethylcyclopentadienyl)ruthenium, the amount of which was 1.0% by weight based on the DER, (1,3-dimethylcyclopentadienyl)(ethylcyclopentadienyl)ruthenium, the amount of which was 1.0% by weight based on the DER, and bis(1,3-dimethylcyclopentadienyl)ruthenium, the amount of which was 1.0% by weight based on the DER) was used as a raw material to conduct film deposition for 0.5 hours using the apparatus of FIG. 1 under the same conditions as in Example 14. The thin film produced was examined by fluorescent X-ray spectroscopy. As a result, a characteristic X-ray line assigned to ruthenium was observed. The film was examined for thickness with an SEM and, as a result, the thickness thereof was found to be 5 nm. An incubation time was calculated from these results and from the results of Example 23, and was found to be 23 minutes.

Comparative Example 1

DER was used as a raw material to conduct film deposition using the apparatus of FIG. 1 under the same conditions as in Example 14. The thin film produced was examined by fluorescent X-ray spectroscopy. As a result, a characteristic X-ray line assigned to ruthenium was observed. The film was examined for thickness with an SEM and, as a result, the thickness thereof was found to be 5 nm.

Comparative Example 2

Figure 5:
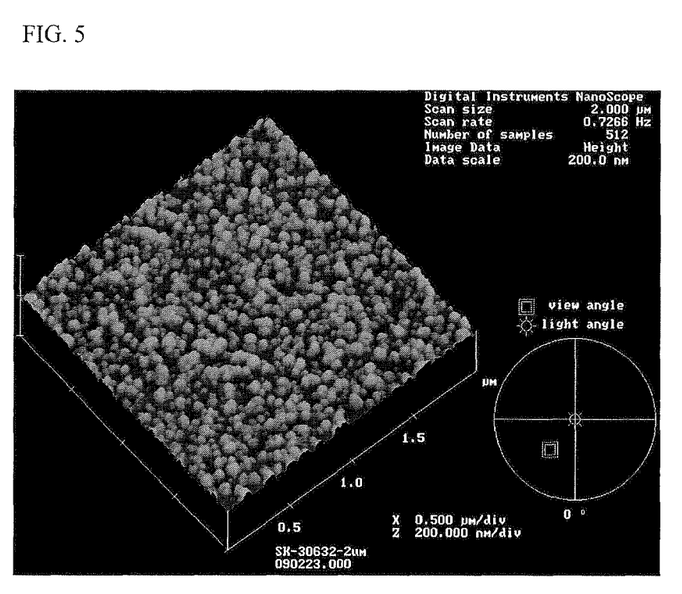
FIG. 5 is a view showing an AFM image of the film obtained in Comparative Example 2.

The ruthenium-containing film produced by the method described in Comparative Example 1 was examined for electrical properties by the four-probe method. As a result, the film was found to be an insulating film. The surface thereof was evaluated with an AFM (FIG. 5). As a result, the surface was found to have an arithmetic mean roughness of 9 nm.

Comparative Example 3

DER was used as a raw material to conduct film deposition using the apparatus of FIG. 1 under the same conditions as in Example 14, except that the substrate temperature was 255° C. The thin film produced was examined by fluorescent X-ray spectroscopy. As a result, a characteristic X-ray line assigned to ruthenium was observed. The film was examined for thickness with an SEM and, as a result, the thickness thereof was found to be 20 nm. The resistivity of the film produced was measured by the four-probe method, and was found to be 2,340 μΩ·cm.

Comparative Example 4

DER was used as a raw material to conduct film deposition for 2 hours using the apparatus of FIG. 1 under the same conditions as in Example 14. The thin film produced was examined by fluorescent X-ray spectroscopy. As a result, a characteristic X-ray line assigned to ruthenium was observed. The film was examined for thickness with an SEM and, as a result, the thickness thereof was found to be 30 nm.

An incubation time was calculated from these results and the results of Comparative Example 1, and was found to be 48 minutes.

The following can be understood from the Examples and Comparative Examples given above.

From a comparison between Comparative Example 1 and Example 14, a comparison between Comparative Example 1 and Example 15, a comparison between Comparative Example 1 and Example 16, and a comparison between Comparative Example 1 and Examples 17-23, it can be seen that the rate of film deposition at a substrate temperature of 240° C. was higher in the case where the ruthenium complex mixtures of the invention were used than in the case where DER was used.

It can also be seen from a comparison between Examples 17-23 and Comparative Example 1 that even when the ruthenium complex mixtures of the invention contain one or more of DER analogue compounds [i.e., bis(ethylcyclopentadienyl)ruthenium, (1,3-dimethylcyclopentadienyl)(ethylcyclopentadienyl)ruthenium, and bis(1,3-dimethylcyclopentadienyl)ruthenium] in a total amount of 5% by weight or less based on the DER, the ruthenium complex mixtures show a far higher film deposition rate than DER.

Furthermore, from a comparison between Comparative Example 2 and Example 24 (comparison between FIG. 5 and FIG. 2), a comparison between Comparative Example 2 and Example 25 (comparison between FIG. 5 and FIG. 3), and a comparison between Comparative Example 2 and Example 26 (comparison between FIG. 5 and FIG. 4), it can be seen that the films produced from the ruthenium complex mixtures of the invention have better surface smoothness than the film produced from DER.

It can be further seen from the comparisons between Comparative Example 2 and Example 24, between Comparative Example 2 and Example 25, and between Comparative Example 2 and Example 26 that the films produced using the ruthenium complex mixtures of the invention have a smaller arithmetic mean roughness than the film produced from DER.

From a comparison between Comparative Example 3 and Example 24, a comparison between Comparative Example 3 and Example 25, a comparison between Comparative Example 3 and Example 26, and a comparison between Comparative Example 3 and Example 27, it can be seen that the films produced at a substrate temperature of 240° C. using the ruthenium complex mixtures of the invention have a lower resistivity than the film produced at a substrate temperature of 255° C. using DER.

Moreover, from a comparison between Comparative Examples 1 and 4 and Examples 23 and 28, it can be seen that the incubation times in the case of using the ruthenium complex mixtures of the invention are shorter than in the case of using DER.

Namely, when the ruthenium complex mixtures of the invention are used, a film having a lower resistivity can be produced at a lower temperature. Furthermore, a ruthenium-containing film can be produced in a shorter period than in the case where DER is used as a raw material.

While the invention has been described in detail and with reference to specific embodiments thereof, it will be apparent to one skilled in the art that various changes and modifications can be made therein without departing from the spirit and scope thereof.

This application is based on a Japanese patent application filed on Dec. 28, 2009 (Application No. 2009-297196) and a Japanese patent application filed on Aug. 9, 2010 (Application No. 2010-178697), the contents thereof being incorporated herein by reference.

INDUSTRIAL APPLICABILITY

The ruthenium complex mixture of the invention can be used as a composition for forming ruthenium-containing films. Use of the mixture as a raw material for film formation renders stable raw-material feeding possible and enables a ruthenium-containing film to be produced at an even lower temperature than in the case where DER is used as a raw material. The ruthenium-containing film obtained has better electrical properties than the ruthenium-containing film produced from DER. Furthermore, it is possible to produce a ruthenium-containing film in a shorter period than the case of using DER as a raw material. Therefore, the invention has a significant industrial value.

DESCRIPTION OF THE REFERENCE NUMERALS

1 Raw-material container
2 Thermostatic chamber
3 Reaction chamber
4 Substrate
5 Reactant gas
6 Diluent gas
7 Carrier gas
8 Mass flow controller
9 Mass flow controller
10 Mass flow controller
11 Vacuum pump
12 Gas discharge

The invention claimed is:

1. A ruthenium complex mixture containing (2,4-dimethylpentadienyl)(ethylcyclopentadienyl)ruthenium and bis(2,4-dimethylpentadienyl)ruthenium, the amount of the latter compound being 0.1-15% by weight based on the (2,4-dimethylpentadienyl)(ethylcyclopentadienyl)ruthenium.

2. The ruthenium complex mixture according to claim 1 containing a compound that is analogous to (2,4-dimethylpentadienyl)(ethylcyclopentadienyl)ruthenium, the amount of the analogous compound being up to 5% by weight based on the (2,4-dimethylpentadienyl)(ethylcyclopentadienyl)ruthenium.

3. A composition for forming a ruthenium-containing film, the composition including the mixture according to claim 1.

4. A method of producing the ruthenium complex mixture according to claim 1, comprising mixing (2,4-dimethylpentadienyl)(ethylcyclopentadienyl)ruthenium with bis(2,4-dimethylpentadienyl)ruthenium, the amount of the latter compound being 0.1-100% by weight based on the (2,4-dimethylpentadienyl)(ethylcyclopentadienyl)ruthenium.

5. A method of producing the ruthenium complex mixture according to claim 1, comprising reacting bis(2,4-dimethylpentadienyl)ruthenium with ethylcyclopentadiene in the presence of zinc and a solvent, the amount of the ethylcyclopentadiene being 0.5-1.0 mol per mole of the bis(2,4-dimethylpentadienyl)ruthenium.

6. The method of producing a ruthenium complex mixture according to claim 5, wherein the bis(2,4-dimethylpentadienyl)ruthenium is bis(2,4-dimethylpentadienyl)ruthenium obtained by reacting 2,4-dimethyl-1,3-pentadiene with halogenated ruthenium represented by general formula [1]

$$RuX_3 \cdot nH_2O \qquad [1]$$

wherein X represents a halogen atom and n indicates 0-10, in the presence of a solvent and zinc.

7. A method of producing a ruthenium-containing film, comprising using the ruthenium complex mixture according to claim 1 as a raw material.

8. A ruthenium-containing film produced by the method according to claim 7.

* * * * *